United States Patent [19]

Baldauf et al.

[11] Patent Number: 5,478,791
[45] Date of Patent: Dec. 26, 1995

[54] NICKEL/ALUMINUM OXIDE CATALYST, PREPARATION THEREOF, USE THEREOF AND HYDROGENATION OF AROMATIC HYDROCARBONS WITH THE AID OF THE CATALYST

[75] Inventors: Wolfgang Baldauf, Dorsten; Martin Rupp, Essen; Heinz Bolz, Gelsenkirchen; Hans-Gerd Lüken, Marl; Joachim Schuler, Marl; Bernd Nowitzki, Marl, all of Germany

[73] Assignee: Huels Aktiengesellschaft, Marl, Germany

[21] Appl. No.: 221,774

[22] Filed: Apr. 1, 1994

[30] Foreign Application Priority Data

Apr. 3, 1993 [DE] Germany .................. 43 10 971.3

[51] Int. Cl.⁶ .................. B01J 21/04; B01J 23/755; B01J 37/18
[52] U.S. Cl. .................. 502/337; 502/325; 502/332; 502/335
[58] Field of Search .................. 502/325, 332, 502/335, 337

[56] References Cited

U.S. PATENT DOCUMENTS 3,870,657  3/1975  Pitzer ........................ 252/464

FOREIGN PATENT DOCUMENTS

| 0086538 | 8/1983 | European Pat. Off. . |
|---|---|---|
| 0092878 | 11/1983 | European Pat. Off. . |
| 0168091 | 1/1986 | European Pat. Off. . |
| 0290100 | 11/1988 | European Pat. Off. . |
| 0349223 | 1/1990 | European Pat. Off. . |
| 0354612 | 2/1990 | European Pat. Off. . |
| 2042166 | 3/1971 | Germany . |
| 2305143 | 8/1974 | Germany . |
| 2946164 | 7/1980 | Germany . |
| 0281081 | 8/1990 | Germany . |
| 0183833 | 10/1984 | Japan . |

OTHER PUBLICATIONS

International Journal of Hydrogen Energy, vol. 17, No. 2, Feb. 1992, Li Qiyuan, "A New Kind of Hydrogen–Producing Catalyst for Hydrocarbon Steam Reforming", pp. 97–100.

*Primary Examiner*—P. Achutamurthy
*Attorney, Agent, or Firm*—Oblon, Spivak, McClelland, Maier, & Neustadt

[57] ABSTRACT

A nickel/aluminum oxide catalyst having a nickel content from 10 to 60% by weight, based on the total catalyst, in which the nickel is in the form of crystallites having an average diameter ranging from 15 nm to 50 nm.

5 Claims, No Drawings

NICKEL/ALUMINUM OXIDE CATALYST, PREPARATION THEREOF, USE THEREOF AND HYDROGENATION OF AROMATIC HYDROCARBONS WITH THE AID OF THE CATALYST

BACKGROUND OF THE INVENTION

1. Field of the Invention

The invention relates to a nickel/aluminum oxide catalyst having a nickel content from 10 to 60% by weight, based on the total catalyst, a process for the preparation thereof and also the use thereof for hydrogenating aromatic hydrocarbons.

In addition, the invention relates to a process for hydrogenating aromatic hydrocarbons with the aid of the catalyst.

2. Discussion of the Background

Mineral oil fractions are used in many areas, such as in the surface coating industry, and as solvents for surface coatings.

Reduction of the aromatics content of the mineral oil fractions allows the isolation of de-aromatized products which are used, for example, in the food industry, pharmaceuticals and even in the cosmetic industry.

Furthermore, aromatics-reduced kerosene can also be used as jet fuel. The reduction in the aromatics content gives advantages, for example in the form of an improved smoke point of the jet fuel.

The lowering of the aromatics content can in general be achieved in a number of ways, as are described, for example, in DE-A 23 05 143. For instance, aromatics-containing hydrocarbons can be de-aromatized by treatment with sulfuric acid or oleum. This technique is, however, problematical because of material attrition by corrosion. Furthermore, handling sulfuric acid or oleum is problematical from the point of view of disposal of the waste sulfuric acid. Another method of reducing the aromatics content is the hydrogenation of the aromatic hydrocarbons with the aid of suitable catalysts. For instance, DE-A 20 42 166 describes catalyst systems for hydrogenating aromatic hydrocarbons using Pt or Rh on catalyst supports. However, such nobel metal catalysts are relatively expensive because of their noble metal content and thus adversely affect the economics of the hydrogenation process.

To make the application of the mineral oil fractions possible, for example in the food industry, the aromatic content of the mineral oil fractions has to be reduced considerably. If the reduction of the aromatics content is to be achieved by catalytic hydrogenation, then lowering the aromatics content to a very low level, for example, in the concentration range of a few ppm by weight, requires large catalyst volumes, which substantially affects the economics of the catalytic hydrogenation process.

DE-A 23 05 143 discloses a catalyst system based on nickel and $Al_2O_3$. The preparation of the catalyst is carried out via the precipitation of nickel/aluminum hydroxycarbonate with various further processing steps. The preparation of the catalyst includes, inter alia, the compounding of the precipitated nickel/aluminum complex with $Al_2O_3$. This process is comparatively complicated. The catalyst thus obtained can be used for hydrogenating aromatic hydrocarbons. However, a residual aromatics content of about 200 ppm by weight still exists in the hydrogenation product after hydrogenation. In addition, the space velocity over the catalyst, expressed in [g of throughput/(cm³ of catalyst.h)], is, at about 1 g/(cm³.h), not very high.

EP-A 0 290 100 describes a catalyst which is prepared by impregnation of a preformed $Al_2O_3$ support with a nickel salt solution. Nickel crystallite sizes of about 2 to 8 nm can be calculated from the features claimed. It is conventionally assumed that nickel catalysts are more active the smaller the crystallite diameter. The catalyst support is pre-treated at high temperatures prior to impregnation, so as to achieve a particular modification of the $Al_2O_3$. The impregnation technique makes it possible to achieve only comparatively low nickel loadings on the catalyst support. In order to increase the nickel content of the catalyst to values of industrial interest, it is necessary to carry out the impregnation of the catalyst a number of times. After each impregnation stage, the catalyst has to be dried or calcined. This process makes the preparation of the catalyst complicated, particularly when high nickel concentrations in the catalyst are to be achieved. When using this catalyst according to EP-A 0 290 100, conversions of 96% in the hydrogenation of aromatic hydrocarbons are only achieved at temperatures of about 150° C. The residual aromatics content in the hydrogenation product is about 7600 ppm by weight under the above-described conditions. At temperatures of about 175° C., the conversion is about 99.4% and the residual aromatics concentration is about 1300 ppm by weights.

EP-A 0 092 878 teaches catalysts containing nickel on $Al_2O_3$, which are likewise used for hydrogenating aromatic hydrocarbons. Nickel crystallite sizes of about 2 to 8 nm are claimed. The preparation of these catalysts is carried out via precipitation of nickel hydroxide on a transition aluminum oxide. This process of preparation is comparatively complicated because of the various sub-steps, particularly when high nickel contents on the catalyst are required, which is the case, for example, if contamination of the catalyst by catalyst poisons cannot be ruled out. A need therefore continues to exist for a nickel catalyst of improved aromatic hydrogenation ability.

SUMMARY OF THE INVENTION

Accordingly, one object of the present invention is to provide a nickel/aluminum oxide catalyst which has a high catalytic activity, makes possible a high space velocity over the catalyst and can be prepared in a simple manner.

Another object of the invention is to provide a nickel catalyst for the catalytic hydrogenation of aromatic hydrocarbons, such that the residual aromatic hydrocarbon content of a hydrogenation product is about 10 ppm by weight or less.

Briefly, these objects and other objects of the present invention as herinafter will become more readily apparent an can be attained by a nickel/aluminum oxide hydrogenation catalyst having a nickel content ranging from 10 to 60% by weight, based on the total catalyst, in which the nickel exists in the form of crystallites which have an average diameter from 15 nm to 50 nm.

In another embodiment of the present invention the nickel/aluminum oxide catalyst is prepared by mixing a nickel compound with an aluminum oxide precursor compound, shaping the mixture, drying the shaped body and the catalyst precursor thus obtained is activated in a hydrogen-containing gas stream at a temperature ranging from 230° to 550° C.

DETAILED DESCRIPTION OF THE PREFERRED EMBODIMENTS

It has now been surprisingly found that a nickel/aluminum oxide catalyst having a nickel content from 10 to 60% by weight and an average nickel crystallite diameter from 15 nm to 50 nm makes possible a very high space velocity over the catalyst and also shows an outstanding catalytic activity. When the present catalyst is used in the catalytic hydrogenation of aromatic hydrocarbons to the corresponding cycloaliphatic compounds, residual aromatic hydrocarbon contents in the hydrogenation product of below 10 ppm by weight can easily be achieved. In addition, the catalyst can be prepared in a particularly simple manner by mixing a nickel compound with an aluminum oxide precursor compound, shaping the mixture, drying the shaped body and activating the catalyst precursor thus obtained in a hydrogen-containing gas stream at temperatures from 230° to 550° C.

Another aspect of the present invention is directed to a process for hydrogenating aromatic hydrocarbons, in the presence of the supported nickel catalyst of the invention.

In the preferred process of the invention for preparing the catalyst, a basic nickel carbonate is mixed with an aluminum oxide precursor compound, the mixture is shaped, the shaped body is dried and the catalyst precursor so obtained is activated in a hydrogen-containing gas stream at temperatures ranging from 230° to 550° C.

In order to improve the miscibility and shapeability of the catalyst composition, the aluminum oxide precursor compound can be pre-treated with a so-called peptizing aid, such as an acid or a base, prior to admixture of the nickel compound. In addition, the moisture content of the mixture can be varied by the addition or removal of water. Likewise from the point of view of improving miscibility and shapeability, customary lubricants such as, for example, graphite, cellulose, cellulose derivatives, and the like can be introduced into the mixtures. The catalyst mixture thus obtained is shaped in a manner known per se. Shaped bodies which can be produced are, inter alia, tablets or else extrudates, each in various geometries such as full cylinders, rings, polyobar structures or the like. Depending on the geometry of the shaped body, the moisture content of the mixture can be varied for the purpose of improving the shapeability of the material of the catalyst.

If desired, the catalyst precursor can, after shaping and drying and prior to its activation, also be subjected to calcination, for example in air or an inert gas such as nitrogen. After activation of the catalyst precursor in a hydrogen-containing gas stream, the catalyst can also be passivated for the purpose of improving handling. The passivation of the catalyst can, for example, be carried out in an inert gas stream which still contains a small amount of an oxidizing gas such as oxygen. The inert gas used can, for example, be nitrogen.

The degree of reduction of the nickel in the catalyst obtained during activation, expressed as the percentage of metallic nickel in the total nickel content of the catalyst, is suitably in the range from 35 to 70%.

The catalytic properties of the catalyst are not altered by any calcination step preceding the activation of the catalyst precursor. For instance, the BET surface area of the catalyst can, independently of a calcination step preceding the activation, be within the range from 100 to 250 m$^2$/g of catalyst.

The catalyst of the invention preferably has a pore volume ranging from 0.3 to 0.75 cm$^3$/g of catalyst. Preferably from 15 to 75% of the pore volume of the catalyst of the invention is accounted for by pores having a diameter of >100 nm, and particularly preferably the catalyst of the invention has the following pore volume distribution:

| Pore diameter (nm) | Proportion of the pore volume (%) |
|---|---|
| ≦2 | 5–15 |
| ≦50 | 20–70 |
| ≦100 | 25–85 |
| >100 | 15–75 |

The catalyst of the invention may contain γ-aluminum oxide and/or η-aluminum oxide and/or boehmite.

Preferably, the fresh catalyst has the following X-ray diffraction pattern:

| Reflection 2 Θ [degrees], CuKα radiation | Reflection width* | Relative intensity [I/I$_0$] |
|---|---|---|
| 14.49 (±0.4) | b | 0–15 |
| 19.4 (±1.2) | vb | 0–10 |
| 26.72 (±0.1) | vn | 0–30 |
| 28.44 (±0.4) | b | 0–15 |
| 37.68 (±0.4) | b to vb | 0–20 |
| 44.75 (±0.2) | n to b | 100 |
| 49.17 (±0.4) | b to vb | 0–15 |
| 52.02 (±0.3) | n to b | 20–40 |
| 54.78 (±0.4) | n to b | 0–10 |
| 63.16 (±1.0) | vb | 5–20 |
| 65.80 (±1.0) | vb | 5–15 |
| 72.14 (±0.4) | b to vb | 0–10 |
| 76.64 (±0.3) | n to b | 10–30 |

*b = broad
vb = very broad
vn = very narrow
n = narrow

Fresh catalyst denotes the catalyst of the invention which is present after activation of the catalyst precursor in the hydrogen-containing gas stream and subsequent pass±vat±on. The process of the invention for hydrogenating aromatic hydrocarbons is preferably carried out at pressures from 5 to 250 bar absolute, and at temperatures from 80° to 300° C. In the hydrogenation process of the invention, the molar ratio of hydrogen to aromatics can suitably be set to from 3 to 500.

Starting materials which are suitable in the hydrogenation process of the invention are, inter alia, aromatic-containing mineral oil fractions having boiling ranges from 20° to 350° C. Thus, aromatic-containing mineral oil fractions having boiling ranges from 20° to 350° C. can be hydrogenated.

The aromatics content of the mineral oil fractions which can be used in the hydrogenation process of the invention is not limited, since, as explained below, overheating of the catalyst of the invention by the liberated heat of reaction is prevented by suitable measures.

The catalyst of the invention can advantageously be divided into separate catalyst beds within the reactor. At suitable positions between the catalyst beds there may be provided devices by means of which cold gas, for example in the form of hydrogen, can be introduced, so as to cool the hot reaction product leaving the catalyst bed upstream of the cold gas introduction. Cold gas is taken to mean a gas whose temperature lies considerably below the temperature of the catalyst beds. The cold gas used is preferably hydrogen or a hydrogen-containing gas mixture. Thus the catalyst of the invention can advantageously be arranged in separate catalyst beds in the reactor and cold gas can be introduced between the beds. In this manner, overheating of the catalyst of the invention by the liberated heat of reaction during continuing hydrogenation in the downstream catalyst bed can be avoided.

At the same time, a comparatively smaller amount of gas containing warmer hydrogen at the inlet to the first catalyst bed makes it possible to more quickly heat up the catalyst of the invention by means of the liberated heat of reaction. Very complete exploitation of the total catalyst bed can thus be achieved. The hydrogen consumed in the hydrogenation of the aromatic hydrocarbons can be replaced by an amount of hydrogen-containing gas so that the molar ratio of hydrogen to aromatics remains constant.

Because of to the build-up of impurities in the hydrogen-containing gas stream, for example, inert gases such as nitrogen, it may be necessary to bleed off a part of the gas stream and to replace it by a gas stream having a higher hydrogen content.

A gas stream containing unconsumed hydrogen can be recirculated. The amount of cold gas introduced to conduct away the heat of reaction depends on the concentration of aromatics in the starting materials.

The sulfur and nitrogen content of the starting material for the hydrogenation process of the invention should preferably be less than 2 ppm by weight.

With the aid of the process of the invention for hydrogenating aromatic hydrocarbons, residual aromatic contents in the hydrogenation product of less than 10 ppm by weight can easily be achieved with simultaneously high space velocity over the catalyst, comparatively low hydrogenation temperatures and high conversions of aromatics.

Obviously, numerous modifications and variations of the present invention are possible in light of the above teachings. It is therefore to be understood that within the scope of the appended claims, the invention may be practiced otherwise than as specifically described herein.

The invention will be now more particularly described by way of example:

EXAMPLE 1

4000 g of aluminum oxide hydroxide hydrate as aluminum oxide precursor compound are moistened with aqueous nitric acid in a mixer so that the preparation has a moisture content, determined by drying for 16 hours at 120° C., of 40%. The nitrate content in the dried product is 3% by weight.

253 g of graphite and 12,116 g of nickel hydroxycarbonate are added to the preparation and all components are intimately mixed with one another. The moisture content of the mixture is adjusted to 40%.

Extrudates in the form of full cylinders are produced from the mixture. After shaping, the shaped bodies are dried at a temperature of 110° C. for 16 hours.

The activation of the catalyst precursor is carried out at a temperature of 400° C. in a mixture of nitrogen as inert gas and hydrogen, the mixing ratio of inert gas to hydrogen being 1:1.

After activation is complete, the catalyst is passivated for the purpose of improving handling by treating with air as the passivating agent at a temperature of about 30° C.

The fresh catalyst so prepared has the following features:
nickel content: 50.3% by weight
nickel crystallite size: 25 nm
BET surface area: 180 m$^2$/g
pore volume: 0.51 cm$^3$/g

| Distribution of the pore volume: | |
|---|---|
| Pore diameter (nm) | Proportion of the pore volume (%) |
| ≤100 | 56 |
| >100 | 44 |

| X-ray diffraction pattern: | | |
|---|---|---|
| Reflection 2Θ [degrees], CuKα radiation | Reflection width* | Relative intensity [I/I$_0$] |
| 14.49 (±0.4) | b | 10 |
| 26.72 (±0.1) | vn | 26 |
| 28.44 (±0.4) | b | 10 |
| 37.68 (±0.4) | b | 16 |
| 44.75 (±0.2) | n to b | 100 |
| 49.17 (±0.4) | b to vb | 11 |
| 52.02 (±0.3) | n to b | 31 |
| 54.78 (±0.4) | b | 7 |
| 63.16 (±1.0) | vb | 12 |
| 65.80 (±1.0) | vb | 10 |
| 72.14 (±0.4) | b to vb | 6 |
| 76.64 (±0.3) | n to b | 20 |

*n = narrow
vn = very narrow
b = broad
vb = very broad

EXAMPLE 2

A catalyst is prepared in an analogous manner to Example 1, with the moisture content of the preparation being adjusted to a value of 37%.

After drying, the catalyst precursor is subjected to a thermal treatment in air at a temperature of 300° C.

The activation of catalyst precursor subsequent to the thermal treatment is carried out as in Example 1, but at a temperature of 350° C. After passivation as in Example 1, a fresh catalyst having the following features is obtained:

| Distribution of the pore volume: | |
|---|---|
| Pore diameter (nm) | Proportion of the pore volume % |
| ≤100 | 59 |
| >100 | 41 |

| X-ray diffraction pattern: | | |
|---|---|---|
| Reflection 2Θ [degrees], CuKα radiation | Reflection width* | Relative intensity [I/I$_0$] |
| 19.4 (±1.2) | vb | 2 |
| 26.8 (±0.1) | vn | 17 |
| 37.63 (±0.4) | b to vb | 9 |
| 44.76 (±0.2) | n to b | 100 |
| 52.11 (±0.3) | n to b | 27 |
| 54.90 (±0.2) | n | 5 |
| 63.80 (±0.6) | vb | 7 |
| 66.66 (±0.4) | b | 10 |
| 76.73 (±0.3) | n to b | 21 |

*n = narrow

-continued

Distribution of the pore volume:

vn = very narrow
b = broad
vb = very broad

EXAMPLE 3

A liquid-phase circulation unit comprising reactor, heat exchanger, separator and pump is charged with a fresh catalyst in accordance with Example 1.

After reactivation of the fresh catalyst with hydrogen at a temperature of about 150° C., 1000 cm$^3$ of $C_{10}$–$C_{24}$-paraffins as starting material are introduced into the unit. The aromatics content of the starting material is 3% by weight, and the boiling range of the starting material extends from a temperature of 190° C. to 275° C. Hydrogenation is carried out at a pressure of 24 bar absolute, a temperature of 140° C. and a molar ratio of hydrogen to aromatics of 223.

After a residence time of 0.5 hours, the residual aromatics content of the hydrogenation product is 9 ppm by weight.

The conversion of aromatics amounts to 99.97% and the space velocity over the catalyst is 2 g/cm$^3$.h.

EXAMPLE 4

57 g of a fresh catalyst in accordance with Example 1 are placed in an integral reactor and reactivated with hydrogen at a temperature of 150° C. Subsequently, a naphtha having an aromatics content of 3% by weight and a boiling range from 52° C. to 286° C. is passed over the catalyst and hydrogenated. The space velocity over the catalyst is 3 g of naphtha/(g of catalyst.h). The molar ratio of hydrogen to aromatics is set to a value of 160. The reaction temperature is 150° C. and the pressure is 30 bar absolute.

A residual aromatics content of 8 ppm by weight remains in the hydrogenation product. The conversion of aromatics is 99.97%.

EXAMPLE 5

A fresh catalyst in accordance with Example 1 is used in a pilot plant having two reactors and two catalyst beds per reactor. After reactivation in a stream of hydrogen at a temperature of 150° C., kerosene having an aromatics content of 22.7% by weight and a boiling range from 116° C. to 287° C. is hydrogenated continuously at a pressure of 150 bar absolute and a space velocity over the catalyst of 4 g of kerosene/(g of catalyst.h).

The molar ratio of hydrogen to aromatics is about 27. After each catalyst bed there is provision for controlling the catalyst temperature by addition of cold gas, in this case hydrogen.

The reactor inlet temperature of the first catalyst bed is 115° C. To control the reaction temperature, hydrogen as cold gas is added between the catalyst beds in an amount such that the reaction temperature rises to a maximum of 190° C. in the downstream catalyst beds. The residual aromatics content of the hydrogenation product is found to be 2 ppm by weight. The conversion of aromatics is >99.999%.

EXAMPLE 6

Example 5 is repeated with a fresh catalyst in accordance with Example 1. However, the starting material used is a naphtha in accordance with Example 4, and no cold gas is added. An addition of cold gas is not required, since no excessive heating of the catalyst is to be expected because of the aromatics concentration of 3% by weight in the starting material. The reactor inlet temperature is 130° C. and the maximum reaction temperature is 165° C.

The hydrogenation product now contains only 1 ppm by weight of aromatics. The conversion of aromatics is >99.99%.

EXAMPLE 7

Example 5 is repeated using a middle petroleum fraction having a boiling range of 50°–165° C. as starting material. The aromatics content in the starting material is 3% by weight. Addition of cold gas is not necessary for the reason mentioned in Example 6.

The hydrogenation product has a residual aromatics content of 1 ppm by weight, and the conversion of aromatics is <99.99%.

What is claimed as new and is desired to be secured by letters patent of the United States is:

1. A nickel/aluminum oxide catalyst having a nickel content of from 10 to 60% by weight, based on the total weight of the catalyst, said nickel being present as crystallites which have an average diameter of from 15 nm to 50 nm, and wherein the catalyst has a pore volume ranging from 0.3 to 0.75 cm$^3$/g, and further wherein from 5–15%, 20–70%, 25–85%, and from 15 to 75% of the pore volume of the catalyst is contributed by pores having a diameter $\leq 2$, $\leq 50$, $\leq 100$ and of greater than 100 nm respectively.

2. A nickel/aluminum oxide catalyst according to claim 1, wherein the aluminum oxide is selected from the group consisting of γ-aluminum oxide, η-aluminum oxide, boehmite and combinations thereof.

3. The nickel/aluminum oxide catalyst according to claim 2, wherein the fresh catalyst has the following X-ray diffraction pattern:

| Reflexion 2Θ [degrees], CuKα radiation | Reflexion width* | Relative intensity [I/I$_0$] |
|---|---|---|
| 14.49 (±0.4) | b | 0–15 |
| 19.4 (±1.2) | vb | 0–10 |
| 26.72 (±0.1) | vn | 0–30 |
| 28.44 (±0.4) | b | 0–15 |
| 37.68 (±0.4) | b to vb | 0–20 |
| 44.75 (±0.2) | n to b | 100 |
| 49.17 (±0.4) | b to vb | 0–15 |
| 52.02 (±0.3) | n to b | 20–40 |
| 54.78 (±0.4) | n to b | 0–10 |
| 63.16 (±1.0) | vb | 5–20 |
| 65.80 (±1.0) | vb | 5–15 |
| 72.14 (±0.4) | b to vb | 0–10 |
| 76.64 (±0.3) | n to b | 10–30 |

*b = broad
vb = very broad
vn = very narrow
n = narrow

4. A process for preparing the nickel/aluminum oxide catalyst according to claim 1, which comprises:

mixing a nickel compound with an aluminum oxide precursor compound;

shaping the mixture into a catalyst body;

drying the shaped catalyst, and then;

activating the catalyst precursor thus obtained in a hydrogen-containing gas stream at temperatures from 230° to 550° C.

5. The process according to claim 4, wherein said nickel compound is a basic nickel carbonate.

* * * * *